US00PP20018P2

(12) United States Plant Patent
Jepsen

(10) Patent No.: US PP20,018 P2
(45) Date of Patent: May 26, 2009

(54) *KALANCHOE* PLANT NAMED 'EVITA'

(50) Latin Name: *Kalanchoe blossfeldiana*
Varietal Denomination: Evita

(75) Inventor: Knud Jepsen, Hinnerup (DK)

(73) Assignee: Knud Jepsen A/S, Hinnerup (DK)

( * ) Notice: Subject to any disclaimer, the term of this patent is extended or adjusted under 35 U.S.C. 154(b) by 0 days.

(21) Appl. No.: 12/006,212

(22) Filed: Dec. 31, 2007

(51) Int. Cl.
*A01H 5/00* (2006.01)

(52) U.S. Cl. ..... Plt./336

(58) Field of Classification Search ..... Plt./336
See application file for complete search history.

*Primary Examiner*—Annette H Para
*Assistant Examiner*—Louanne C Krawczewicz Myers
(74) *Attorney, Agent, or Firm*—C. A. Whealy

(57) ABSTRACT

A new and distinct cultivar of *Kalanchoe* plant named 'Evita', characterized by its large to medium size, upright, uniform and moderately vigorous growth habit; large dark green-colored leaves; uniform and freely flowering habit; large double white-colored flowers; and excellent postproduction longevity.

1 Drawing Sheet

Botanical designation: *Kalanchoe blossfeldiana.*
Cultivar denomination: 'Evita'.

BACKGROUND OF THE INVENTION

The present invention relates to a new and distinct cultivar of *Kalanchoe,* botanically known as *Kalanchoe blossfeldiana,* and hereinafter referred to by the name 'Evita'.

The new *Kalanchoe* is a product of a planned breeding program conducted by the Inventor in Hinnerup, Denmark. The objective of the breeding program is to create new double-flowered *Kalanchoe* cultivars with attractive foliage and flower coloration.

The new *Kalanchoe* originated from a cross-pollination made by the Inventor in Hinnerup, Denmark in April, 2005, of the *Kalanchoe blossfeldiana* cultivar KJ 2003-0682, not patented, as the female, or seed parent with the *Kalanchoe blossfeldiana* cultivar Simone 2000, disclosed in U.S. Plant Pat. No. 12,319, as the male, or pollen, parent. The cultivar Evita was discovered and selected by the Inventor as a flowering plant from within the progeny of the stated cross-pollination in a controlled environment in Hinnerup, Denmark in November, 2005.

Asexual reproduction of the new *Kalanchoe* by vegetative terminal cuttings in a controlled environment in Hinnerup, Denmark since May, 2006, has shown that the unique features of this new *Kalanchoe* are stable and reproduced true to type in successive generations.

SUMMARY OF THE MENTION

The cultivar Evita has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Evita'. These characteristics in combination distinguish 'Evita' as a new and distinct cultivar of *Kalanchoe:*

1. Large to medium in size, upright, uniform and moderately vigorous growth habit.
2. Large dark green-colored leaves.
3. Uniform and freely flowering habit.
4. Large double white-colored flowers.
5. Excellent postproduction longevity.

Plants of the new *Kalanchoe* can be compared to plants of the female parent, the cultivar KJ 2003-0682. Plants of the new *Kalanchoe* differ from plants of the cultivar KJ 2003-0682 primarily in petal quantity as plants of the new *Kalanchoe* have flowers with more petals than plants of the cultivar KJ 2003-0682.

Plants of the new *Kalanchoe* can also be compared to plants of the male parent, the cultivar Simone 2000. Plants of the new *Kalanchoe* differ from plants of the cultivar Simone 2000 in the following characteristics:

1. Plants of the new *Kalanchoe* are not as vigorous as plants of the cultivar Simone 2000.
2. Plants of the new *Kalanchoe* have double flowers whereas plants of the cultivar Simone 2000 have single flowers.
3. Plants of the new *Kalanchoe* have larger flowers than plants of the cultivar Simone 2000.

Plants of the new *Kalanchoe* can be compared to plants of the *Kalanchoe blossfeldiana* cultivar Grace, disclosed in U.S. Plant Pat. No. 19,271. In side-by-side comparisons conducted in Hinnerup, Denmark, plants of the new *Kalanchoe* differed from plants of the cultivar Grace in the following characteristics:

1. Plants of the new *Kalanchoe* had fewer petals per flower than plants of the cultivar Grace.
2. Plants of the new *Kalanchoe* flowered about one week later than plants of the cultivar Grace.

BRIEF DESCRIPTION OF THE PHOTOGRAPHS

The accompanying colored photographs illustrate the overall appearance of the new *Kalanchoe,* showing the colors as true as it is reasonably possible to obtain in colored reproductions of this type. Colors in the photographs may differ slightly from the color values cited in the detailed botanical description which accurately describe the colors of the new *Kalanchoe*.

The photograph at the top of the sheet comprises a side perspective view of a typical flowering plant of 'Evita' grown in a container.

The photograph at the bottom of the sheet comprises closeup views of typical generative and vegetative leaves, upper and side perspective view of typical flowers and a typical flowering stem of 'Evita'.

DETAILED BOTANICAL DESCRIPTION

The aforementioned photographs and following observations, measurements and values describe plants grown in Hinnerup, Denmark in a glass-covered greenhouse during the late summer and under conditions which closely approximate commercial production. During the production of the plants, day temperatures were about 19° C., night temperatures were about 21° C. and light levels ranged from 10 kilolux to 50 kilolux. Unrooted cuttings were directly stuck in 10-cm containers and received long day/short night conditions (more than 14 hours of light) for about two weeks; plants then received photoinductive short day/long night conditions (minimum 14 hours darkness) until flowering. Plants were about 16 weeks old when the photographs and the description were taken. In the detailed description, color references are made to The Royal Horticultural Society Colour Chart, 2001 Edition, except where general terms of ordinary dictionary significance are used.

Botanical classification: *Kalanchoe blossfeldiana* cultivar Evita.

Parentage:

*Female, or seed, parent.*—*Kalanchoe blossfeldiana* cultivar KJ 2003-0682, not patented.

*Male or pollen parent.*—*Kalanchoe blossfeldiana* cultivar Simone 2000, disclosed in U.S. Plant Pat. No. 12,319.

Propagation:

*Type.*—By vegetative terminal cuttings.

*Time to initiate roots, summer.*—About two weeks at temperatures of 19° C. to 21° C.

*Time to initiate roots winter.*—About three weeks at temperatures of 19° C. to 21° C.

*Time to produce a rooted young plant, summer.*—About three weeks at temperatures of 19° C. to 21° C.

*Time to produce a rooted young plant, winter.*—About 24 days at temperatures of 19° C. to 21° C.

*Root description.*—Fine, fibrous; white in color.

*Rooting habit.*—Freely branching; moderately dense.

Plant description:

*Plant habit.*—Upright, uniform and moderately vigorous growth habit. Very freely flowering with numerous compound cymes. Inverted triangle with rounded crown. Appropriate for 9-cm to 13-cm containers.

*Plant height at flowering.*—About 22 cm to 26 cm.

*Plant diameter at flowering.*—About 22 cm to 24 cm.

*Branching habit.*—Usually about two to six lateral branches develop per plant. Pinching (removal of the terminal apex) is not required but will enhance lateral branch development.

Lateral branch description:

*Length.*—About 10 cm to 14 cm.

*Diameter.*—About 5 mm.

*Internode length.*—About 1 cm to 2.5 cm.

*Aspect.*—Erect.

*Strength.*—Strong.

*Texture.*—Smooth, glabrous.

*Color.*—147B.

Foliage description:

*Arrangement.*—Opposite, simple; generally symmetrical.

*Length, vegetative plants.*—About 9 cm to 14 cm.

*Width, vegetative plants.*—About 6 cm to 9 cm.

*Length, generative plants.*—About 2 cm to 14 cm.

*Width, generative plants.*—About 1 cm to 9 cm.

*Shape.*—Ovate.

*Apex.*—Rounded.

*Base.*—Obtuse with attenuate tendencies.

*Margin.*—Crenate.

*Texture, upper and lower surfaces.*—Glabrous, leathery; succulent.

*Venation pattern.*—Pinnate.

*Color.*—Developing foliage, upper surface: 136A. Developing foliage, lower surface: 147B. Fully expanded foliage, upper surface: 136A; venation, 136A. Fully expanded foliage, lower surface: 147B; venation, 147B.

*Petiole.*—Length: About 2 cm. Diameter: About 5 mm to 8 mm. Texture, upper and lower surfaces: Smooth, glabrous. Color, upper surface: 136A. Color, lower surface: 147B.

Flower description:

*Flower arrangement and habit.*—Double flowers arranged singly in compound dichasial cymes that arise from leaf axils. Uniform and freely flowering habit with usually about 13 to 28 flowers per inflorescence. Flowers not persistent. Flowers not fragrant.

*Natural flowering season.*—Plants of the new *Kalanchoe* initiate and develop flowers under short day/long night conditions or during the late autumn/winter/early spring. Flower initiation and development can also be induced under artificial short day/long night conditions (at least 14 hours of darkness).

*Time to flower.*—Under short day/long night photoinductive conditions, about 79 days are required. Actual time to flower is primarily dependent upon temperature and light intensity.

*Post-production longevity.*—Excellent post-production longevity; plants maintain good foliage and flower substance for about six weeks under interior environmental conditions.

*Inflorescence height.*—About 10 cm to 15 cm.

*Inflorescence diameter.*—About 3 cm to 8 cm.

*Flower diameter.*—About 2.8 cm.

*Flower length (height).* About 1 cm.

*Flower bud.*—Shape: Ovoid. Length: About 1.5 cm. Diameter: About 8 mm. Color: 157A tinted with 149A.

*Petals.*—Arrangement: About 20 fused at the base. Length (largest petals): About 1.5 cm. Width (largest petals): About 1.1 cm. Aspect: Slightly upright to eventually recurved. Shape: Rounded to ovate. Apex: Acute to obtuse. Margin: Entire. Texture, upper and lower surfaces: Smooth, glabrous. Color: When opening, upper surface: 160B. When opening, lower surface: 157A slightly tinted with 149A. Fully opened, upper surface: 155B. Fully opened, lower surface: 155C slightly tinted with 149A.

*Sepals.*—Appearance: Four fused at the base. Length: About 8 mm. Width: About 2 mm. Shape: Lanceolate. Apex: Acute. Base: Truncate. Margin: Entire. Texture, upper and lower surfaces: Smooth; glabrous. Color, immature, upper surface: 146A. Color, immature, lower surface: 149A. Color, mature, upper and lower surfaces: 149A.

*Peduncles.*—Length: About 1 cm to 6 cm. Diameter: About 2 mm to 4 mm. Aspect: Erect to about 60° from vertical. Strength: Strong. Texture: Smooth, glabrous. Color: 147B.

*Pedicels.*—Length: About 2 mm to 5 mm. Diameter: About 1 mm to 2 mm. Aspect: Erect to about 90° from vertical. Strength: Strong. Texture: Smooth, glabrous. Color: 147B.

*Reproductive organs.*—Androecium: Stamen number: About five to ten per flower. Anther shape: Elliptic to oblong. Anther size: About 1 mm by 1 mm. Anther color: Close to 20B. Amount of pollen: Scarce. Pollen color: Close to 20A. Gynoecium: Pistil number: About three to five per flower. Pistil length: About 9 mm. Style length: About 8 mm. Style color: 145A. Stigma shape: Round. Stigma color: 145A. Ovary color: Close to 144B.

*Seed.*—Quantity per flower: About 40. Length: Less than 1 mm. Diameter: Less than 1 mm. Color: 145C.

Temperature tolerance: Plants of the new *Kalanchoe* have been observed to tolerate temperatures from about 5° C. to about 30° C.

Pathogen/pest resistance: Plants of the new *Kalanchoe* have not been observed to be resistant to pests and pathogens common to *Kalanchoes*.

It is claimed:

1. A new and distinct *Kalanchoe* plant named 'Evita' as illustrated and described.

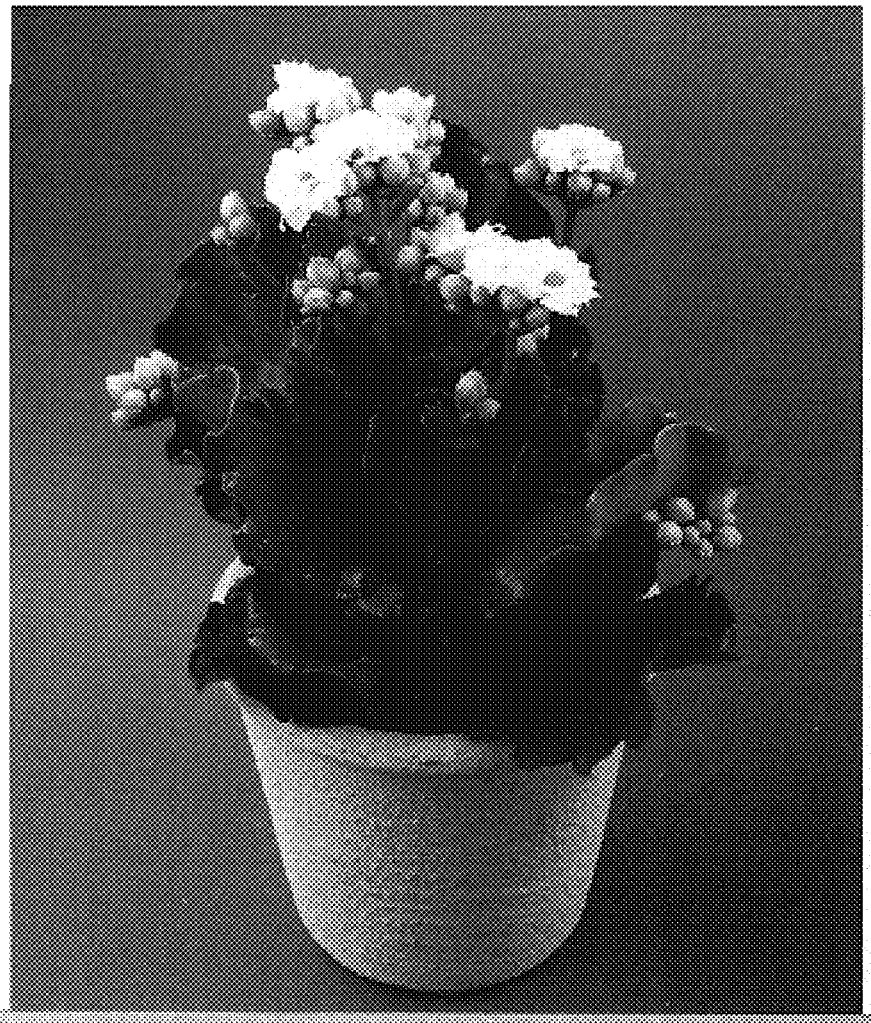
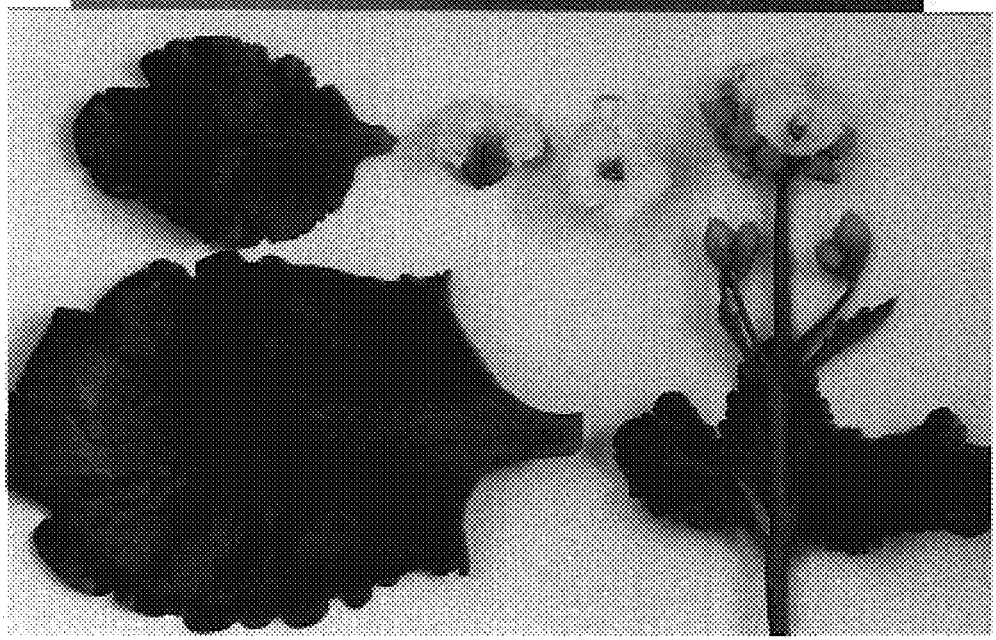

* * * * *